US007261813B2

(12) United States Patent  (10) Patent No.: US 7,261,813 B2
Marcus et al.  (45) Date of Patent: Aug. 28, 2007

(54) MONOLITHIC STRUCTURES COMPRISING POLYMERIC FIBERS FOR CHEMICAL SEPARATION BY LIQUID CHROMATOGRAPHY

(75) Inventors: Richard Kenneth Marcus, Clemson, SC (US); Rayman Dupre Stanelle, Seneca, SC (US)

(73) Assignee: Clemson University, Clemson, SC (US)

( * ) Notice: Subject to any disclaimer, the term of this patent is extended or adjusted under 35 U.S.C. 154(b) by 278 days.

(21) Appl. No.: 10/915,735

(22) Filed: Aug. 10, 2004

(65) Prior Publication Data

US 2006/0032816 A1  Feb. 16, 2006

(51) Int. Cl.
  *B01D 15/08* (2006.01)
(52) U.S. Cl. .............................. 210/198.2; 210/502.1; 210/510.1; 210/635; 210/638; 210/656
(58) Field of Classification Search ............. 210/198.2, 210/635, 638, 656, 500.23, 502.1, 510.1
See application file for complete search history.

(56) References Cited

U.S. PATENT DOCUMENTS

| 3,269,817 | A | * | 8/1966 | Bondley ..................... 65/393 |
| 4,111,815 | A | | 9/1978 | Walker et al. |
| 4,187,333 | A | | 2/1980 | Rembaum et al. |
| 4,286,005 | A | | 8/1981 | Berger |
| 4,354,889 | A | | 10/1982 | Berger |
| 4,391,716 | A | | 7/1983 | McCurry |
| 4,657,742 | A | | 4/1987 | Beaver |
| 4,729,808 | A | | 3/1988 | Berger |
| 4,957,620 | A | | 9/1990 | Cussler |
| 4,996,107 | A | | 2/1991 | Raynolds et al. |
| 5,184,192 | A | | 2/1993 | Gilby et al. |
| 5,225,079 | A | * | 7/1993 | Saito et al. ............ 210/321.61 |
| 5,234,594 | A | | 8/1993 | Tonucci et al. |
| 5,266,197 | A | * | 11/1993 | Takata et al. .......... 210/500.23 |

(Continued)

FOREIGN PATENT DOCUMENTS

WO  WO 03022393 A1  3/2003

OTHER PUBLICATIONS

Article—*A capillary-scale liquid chromatography system that improves the practical sensitivity of HPLC-MS (MS) analysis*, Steven Cohen and Brian J. Murphy, Mar. 1999, pp. 28-32.

(Continued)

*Primary Examiner*—Ernest G. Therkorn
(74) *Attorney, Agent, or Firm*—Dority & Manning, P.A.

(57) ABSTRACT

Monolithic cartridges including a plurality of nominally aligned polymer fibers can be used as stationary phase materials for liquid chromatography separations. Bundles of fibers are packed together so as to form capillary channels between the fibers. Different polymer compositions permit the "chemical tuning" of the separation process. The fibers can be physically or chemically bonded at spaced locations throughout the cartridge or can be packed together under pressure by use of an encasing wrap to form the capillary channels. Use of fibers allows a wide range of liquid flow rates with very low backpressures. Applications in HPLC, cap-LC, prep-scale separations, analytical separations, waste remediation/immobilization, extraction of selected organic molecules/ions from solution, purification of liquid streams (process waste, drinking water, pure solvents), selective extraction of cell matter and bacteria from growth media, and immobilization of cell matter and bacteria are envisioned.

27 Claims, 17 Drawing Sheets

U.S. PATENT DOCUMENTS

| | | | |
|---|---|---|---|
| 5,277,821 | A | 1/1994 | Coughlin et al. |
| 5,604,012 | A | 2/1997 | Okamoto et al. |
| 5,695,702 | A * | 12/1997 | Niermeyer ................ 264/129 |
| 5,800,897 | A | 9/1998 | Sharma et al. |
| 5,855,798 | A | 1/1999 | Phillips et al. |
| 5,858,065 | A * | 1/1999 | Li et al. ......................... 95/45 |
| 5,961,678 | A | 10/1999 | Pruette et al. |
| 5,972,505 | A | 10/1999 | Phillips et al. |
| 6,270,674 | B1 | 8/2001 | Baurmeister et al. |
| 6,616,723 | B2 | 9/2003 | Berger |
| 6,656,360 | B2 | 12/2003 | Rohrbach et al. |
| 2001/0035093 | A1* | 11/2001 | Yokota ............................. 96/8 |
| 2004/0020845 | A1* | 2/2004 | Suzuki et al. .......... 210/500.23 |
| 2005/0023221 | A1 | 2/2005 | Marcus |

OTHER PUBLICATIONS

Article—*A Novel Stationary Phase: Capillary-Channeled Polymer (C-CP) Fibers for HPLC Separations of Proteins,* Dwella K. Nelson and R. Kenneth Marcus, Journal of Chromatographic Science, vol. 41, Oct. 2003, pp. 475-479.

Article—*Capillary-channeled polymer fibers as stationary phases in liquid chromatography separations,* R. Kenneth Marcus, W. Clay Davis, Brad C. Knippel, LaTasha LaMotte, Teresa A. Hill, Dvora Perahia, and J. David Jenkins, Journal of Chromatography A, vol. 986, 2003, pp. 17-31.

* cited by examiner

MONOLITHIC STRUCTURES COMPRISING POLYMERIC FIBERS FOR CHEMICAL SEPARATION BY LIQUID CHROMATOGRAPHY

BACKGROUND OF THE INVENTION

The present invention relates to chemical analysis and cleansing of liquid streams and more particularly to liquid chromatography and wastewater treatment.

At present, liquid-phase chemical separations are usually performed in "columns" prepared by the packing of metal tubes with spherical beads that are composed of either silica or polystyrene and have diameters of 3 to 50 µm. The more or less inert beads provide solid supports that are chemically modified to produce a surface having targeted chemical characteristics. For example, in performing reversed-phase liquid chromatography, long carbon chains (C-18) can be affixed to the surfaces of the beads so as to produce a hydrophobic surface for the separation of non-polar organics. In some systems, beads can include particular surface polymers upon formation, precluding the necessity of post-formation modification of the materials.

Effective separations require dense packing of the beads into these columns to avoid dead-volume, which is any location within the column where turbulence can occur and interactions between molecules in the liquid and the surfaces of the beads are minimal. As a consequence of dense packing, high driving pressures (e.g., 2,000 to 5,000 psi) are required to overcome the backpressures that otherwise would prevent the liquid phase from moving through the densely packed columns.

Alternatively, highly porous "monoliths" are formed within the columns to generate high surface areas for interaction with the species that flow through the columns. Here, the high backpressures and a limited set of stationary phase chemistries can be restrictive. In the case of so-called "prep-scale" separations, the capital costs associated with producing large volume columns and the demands on the system hydraulics (i.e. pumps) are very high.

SUMMARY OF THE INVENTION

The present invention is generally directed to devices and methods for separation of species from a liquid mixture. For instance, in one embodiment, the invention is directed to a separation device comprising a monolithic cartridge that can be utilized for separating species from a mixture, for example as the stationary phase of a separation column in a high performance liquid chromatography (HPLC) process. In other embodiments, the devices may be useful in cap-LC, prep-scale separations, analytical separations, waste remediation/immobilization, extraction of selected organic molecules/ions from solution, purification of liquid streams (process waste, drinking water, pure solvents), selective extraction of cell matter and bacteria from growth media, or immobilization of cell matter and bacteria.

In general, the monolithic cartridges of the invention can include a plurality of nominally aligned polymeric fibers and can define capillaries between adjacent fibers such that the cartridge can exhibit macro-capillarity or bulk wicking action across the cartridge.

In one embodiment, at least a portion of the fibers in the cartridge can be bonded to adjacent fibers. For example the fibers can be physically, chemically, or pressure bonded at locations where adjacent fibers contact one another. In one particular embodiment, the fibers can be heat bonded at spaced locations throughout the monolithic cartridge.

Optionally, the monolithic cartridge can include a wrap that surrounds the fibers of the cartridge that can be disposed along the axial length of the aligned fibers. In one particular embodiment, a wrap surrounding the fibers can exert suitable radial pressure upon the fibers so as to press the individual fibers together and form capillaries between adjacent fibers without the necessity of physically or chemically bonding the fibers together. In one particular embodiment, wherein a fluid can be forced through the cartridge under pressure, the monolithic cartridge can include a wrap surrounding the fibers that comprises a nonporous material.

The polymeric fibers of the monolithic cartridges can be formed of any suitable polymeric material and can be of any suitable cross-sectional shape and size. For example, in one embodiment, the fibers can be nominally circular in cross-section. In another embodiment, the fibers can be configured with co-linear channels that run the length of the surface of each fiber. In addition, the monolithic cartridge can include a mix of different fibers. For instance, the monolithic cartridge can include fibers of different materials and/or different cross-sectional shapes and sizes.

If desired, the fibers can be modified so as to exhibit enhanced reactivity. In one embodiment, the fibers can be modified to exhibit enhanced attraction for a molecular species or family thereof that can be separated from a liquid during the process. For example, the fibers can be modified by protonation of the fibers, the addition of a chemical reactivity to the fibers, or through alteration of the hydrophobicity or ionic character of the fibers.

In another embodiment, the invention is directed to methods of separating a species from a fluid. For example, a fluid containing at least one molecular species can be moved through the capillaries of a monolithic cartridge, and the species can be separated from the fluid by chemical attachment of the species to the polymeric fibers in the cartridge.

The fluid can be moved through the cartridge according to any suitable method. For example, in one embodiment, the fluid can be pumped through the cartridge under pressure or can be moved through the cartridge via electro-osmosis methods as are generally known in the art. In another embodiment, the fluid can be moved through the cartridge by only the macro-level wicking action of the capillaries between the fibers. In another embodiment, the fibers can include surface-channeled fibers, and the monolithic cartridge can exhibit both micro-level wicking action through the surface-channels of the individual fibers as well as macro-level bulk wicking action through the capillaries between adjacent fibers.

In another embodiment, the disclosed invention is directed to a method for separating a mixture containing two or more proteins. In particular, it has been discovered that the channeled polymer fibers and monolithic cartridges disclosed herein can be utilized to separate biological macromolecular species such as proteins from a fluid.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures, in which.

The same numerals designate the same or like components throughout the drawings and description.

DETAILED DESCRIPTION

Reference will now be made in detail to various embodiments of the invention, one or more examples of which are illustrated in the accompanying drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents.

Figures 1, 1A:
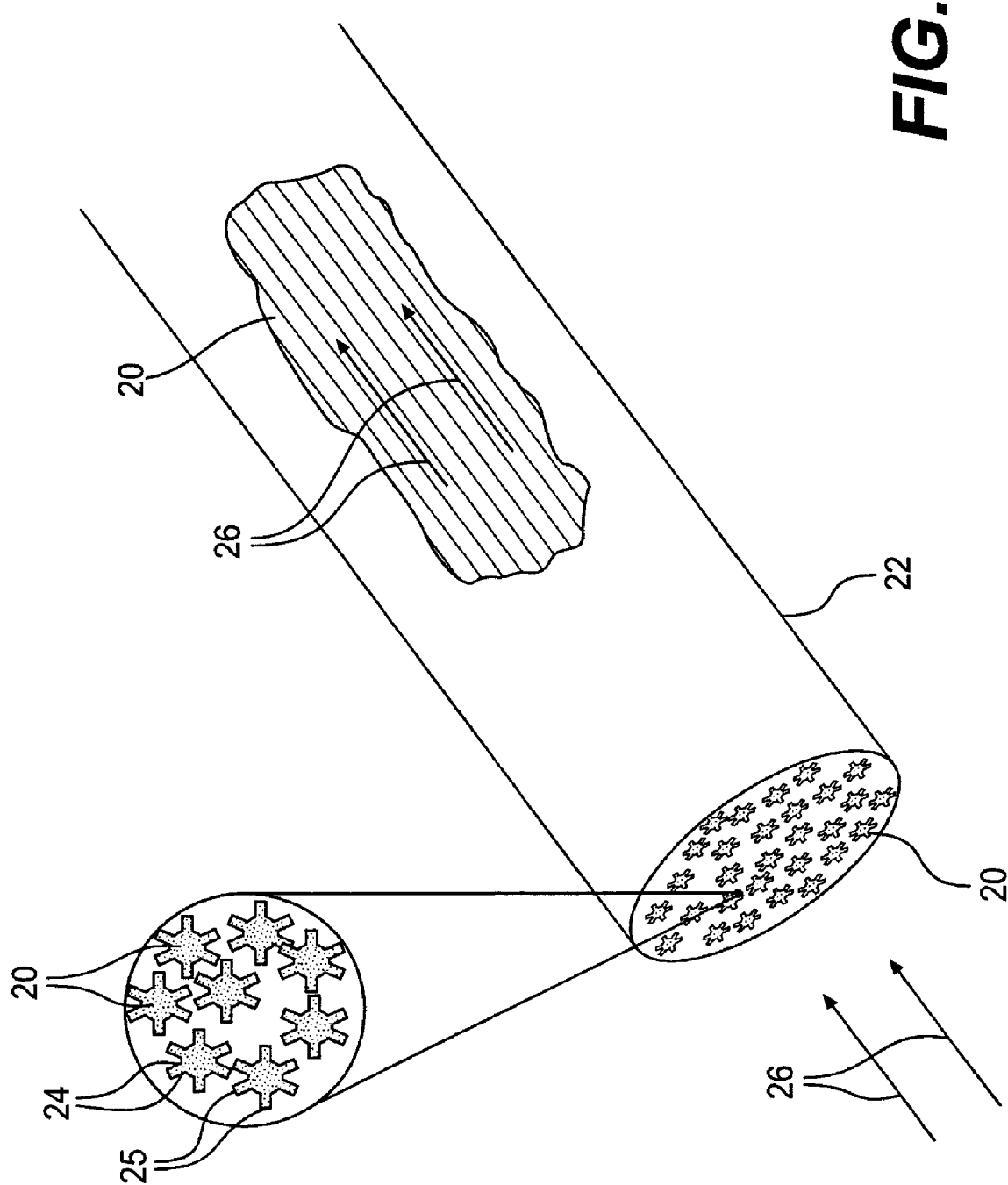
FIG. 1 is a cross-sectional representation of a liquid analyte flowing through channeled fibers placed in a single column formed by a 0.25-inch (about 4.5 mm) diameter tube.
FIG. 1A is an expanded view window showing the end-on shape of the fibers and the potential irregular packing of the fibers in the column of FIG. 1.

As shown in FIG. 1, bundles of surface-channeled polymer fibers 20 are packed into a column 22 that is formed by a tube having a uniform circular inside diameter of 0.25 inches and a length of 12 inches. The dimensions of the column 22 can be any size that is used in the practice of chromatography. Desirably, the length of each fiber 20 is substantially the same as the length of the column 22 and is disposed to extend within the column 22 over substantially the entire length of the column 22. However, fibers 20 that have lengths that are shorter than the length of the column 22 may be used, but are not preferred. Moreover, an individual column can include fibers of various lengths.

FIG. 1 also includes an inset at 1A that illustrates one possible embodiment of the surface-channel fibers. As shown schematically in cross-section in the expanded view window of FIG. 1A, each fiber strand 20 has six co-linear channels 24 extending the entire length of the exterior surface of the fiber 20. Each channel 24 is defined by a pair of opposed walls 25 that extend generally and longitudinally and form part of the exterior surface of the fiber 20. Desirably, these channels 24 and walls 25 extend down the entire length of the fiber 20 parallel to the longitudinal axis of the fiber 20 and are nominally co-linear on each fiber 20. This produces de facto substantially the same co-linear channels 24 along the entire length of the column 22. It should be understood that the particular shape of the embodiment of the surface-channeled fibers illustrated in FIGS. 1 and 1A is not a requirement of the present invention. For instance, the number and/or cross-sectional shape of the channels can vary from that shown in the figures in other embodiments.

In an alternative embodiment, the channels 24 can be configured to wrap around the length of the fiber 20 in a helical fashion. However, as substantially all of the channels 24 can be nominally co-linear on each fiber 20, substantially all of the channels 24 of the fibers 20 within each column 22 can follow a helix pattern that has the same pitch. The pitch is the number of complete turns of the channel 24 around the circumference of the fiber 20 per unit of length of the fiber 20. This also produces de facto substantially the same co-linear channels 24 along the entire length of the column 22.

Additionally, in the course of packing the fibers 20 into a bundle that lays along the entire length of the column 22, whether the individual fibers have purely linear channels 24 or helical ones, it is possible that one or more, even all, of the fibers 20 in the bundle will rotate about its/their own axis or the axis of the column 22 over the entire length of the column. In other words, the surface-channeled fibers 20 may twist as they lay from one end of the column 22 to the opposite end. Accordingly, the channels 24 and walls 25 also may twist somewhat.

In some embodiments of the present invention, a device can be provided to move fluid through the column 22 and thus through the channels 24 of the fibers 20. A pump (not shown) is typically provided for this purpose. The flow of liquid through the column 22 is schematically indicated by the arrows designated by the numeral 26 in FIG. 1. A portion of the column 22 is cut away in the view shown in FIG. 1 for the purpose of illustrating the flow of liquid 26 through the column 22 along the fibers 20 arranged with their longitudinal axes parallel to the longitudinal axis of the column 22. The nominal diameter of each fiber 20 desirably ranges 10 to 80 micrometers.

In general, any method for moving the fluid through the column 22 as is generally known in the art may be utilized. For example, in other embodiments, electro-osmosis or any other suitable hydro-dynamic means may be utilized to move fluid through the column 22.

However, in some applications, the movement of the fluid may be effected without a device that is separate from the fibers themselves. In such embodiments, the fluid can, in one embodiment, move through the channels 24 of the fibers 20 solely by capillary action of the channels 24 of the fibers 20. In other embodiments of the invention, discussed in detail below, the fluid can move through the column with macro-level capillary action between the fibers in addition to or alternative to the micro-level capillary action through the channels 24 of the individual fibers 20.

Advantageous in the use of these channeled polymer fibers 20 as stationary phase materials, as compared to fibers having a more circular cross-sectional shape, is their higher surface area-to-volume ratios. Moreover, the shape and the number of channels 24 can be dependent on achieving the desired attribute of very high surface area-to-volume ratios. In this regard, helical channels 24 can pack more surface area than linear channels 24 and thus may be preferred, in some embodiments.

Another advantage of using channeled polymer fibers 20 in the disclosed processes is the fact that they generate very low backpressures (e.g., 500 to 1500 psi for linear channels 24 for normal chromatography flow rates (0.5 to 3 mL/min). The lower backpressure produced in the column 22 containing channeled polymer fibers 20 relative to the backpressure produced in the conventional column containing beads, is believed to be due to the parallel-running channels 24. The ability to use fibers 20 of any desired length, while encountering relatively low backpressures, would suggest great potential for using columns 22 of these channeled polymer fibers 20 in prep-scale separations or for waste remediation in a variety of industries.

There are different fabrication approaches to form channeled polymer fibers 20 of the sort demonstrated here. In general, the process used to make these channeled, polymer fibers 20 is amenable to any polymers that can be spin-melted. For example, channeled fibers 20 may be melt spun from any of a number of different polymer precursors. A non-limiting list of exemplary materials from which the fibers of the invention can be formed can include polypropylene precursors, polyester precursors, polyaniline precursors, precursors composed of polylactic acid, and nylon precursors. Moreover, it should be understood that the polymeric fibers of the present invention can include surface-channeled fibers as well as fibers of other cross-sectional shapes, as will be discussed in more detail below. In general use, these channeled polymer fibers 20 tend to have a very strong wicking action for a variety of liquids, including water.

The ability to perform chemical separation of otherwise similar compounds for mixtures of polyaromatic hydrocarbons (PAHs), lipids, and organic and inorganic lead compounds has been demonstrated. This capability is particularly surprising given these seemingly chemically benign polymer compositions.

In one embodiment, the materials and devices of the present invention can be utilized for separations of mixtures containing macromolecular compounds, including biological macromolecular compounds. For example, separations of mixtures of proteins can be performed with the disclosed materials and devices.

Figure 2A:
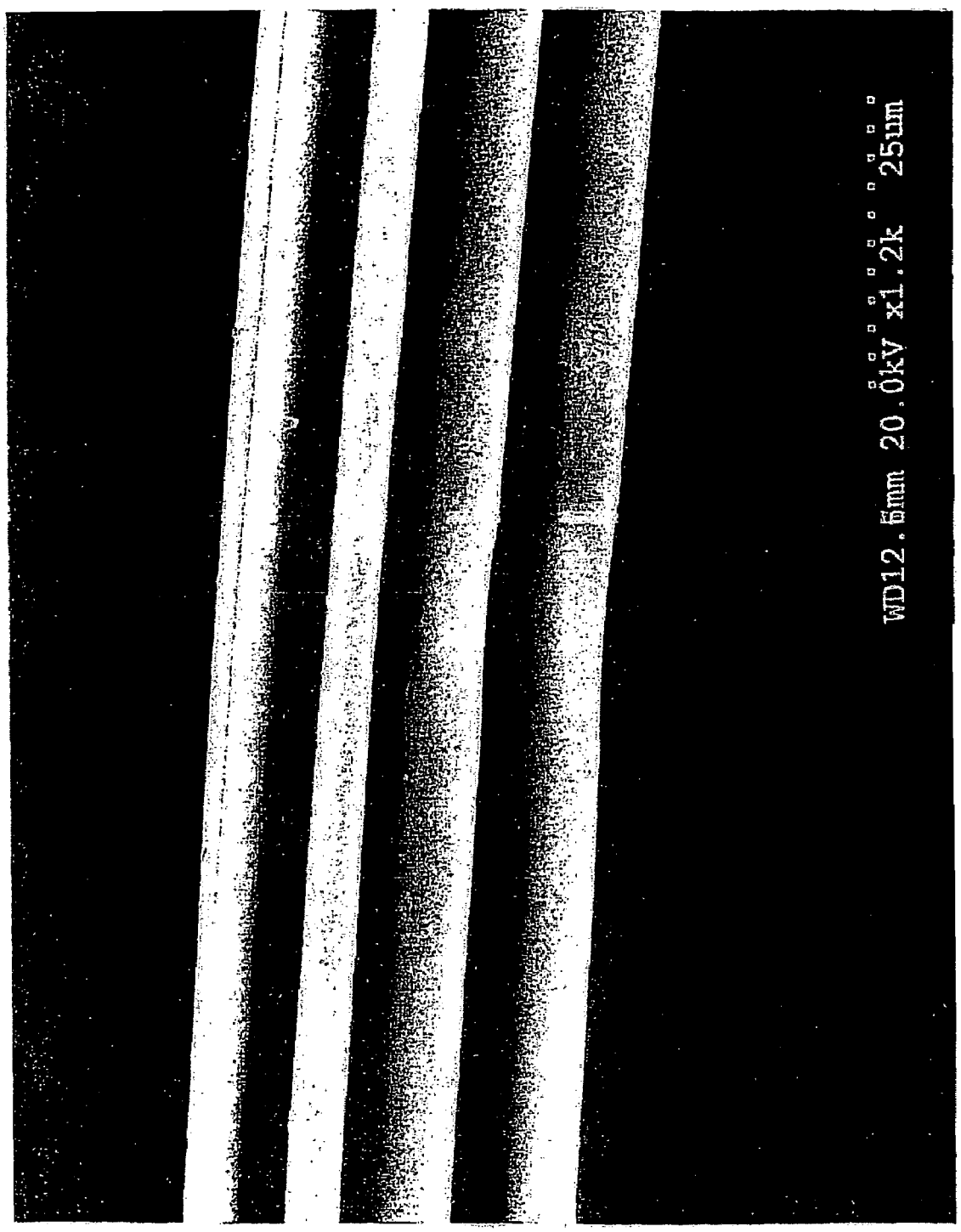
FIG. 2A is a micrograph of an enlarged side view of an intermediate portion of a channeled polyester fiber such as may be used in a column of a chromatograph.
Figure 2B:
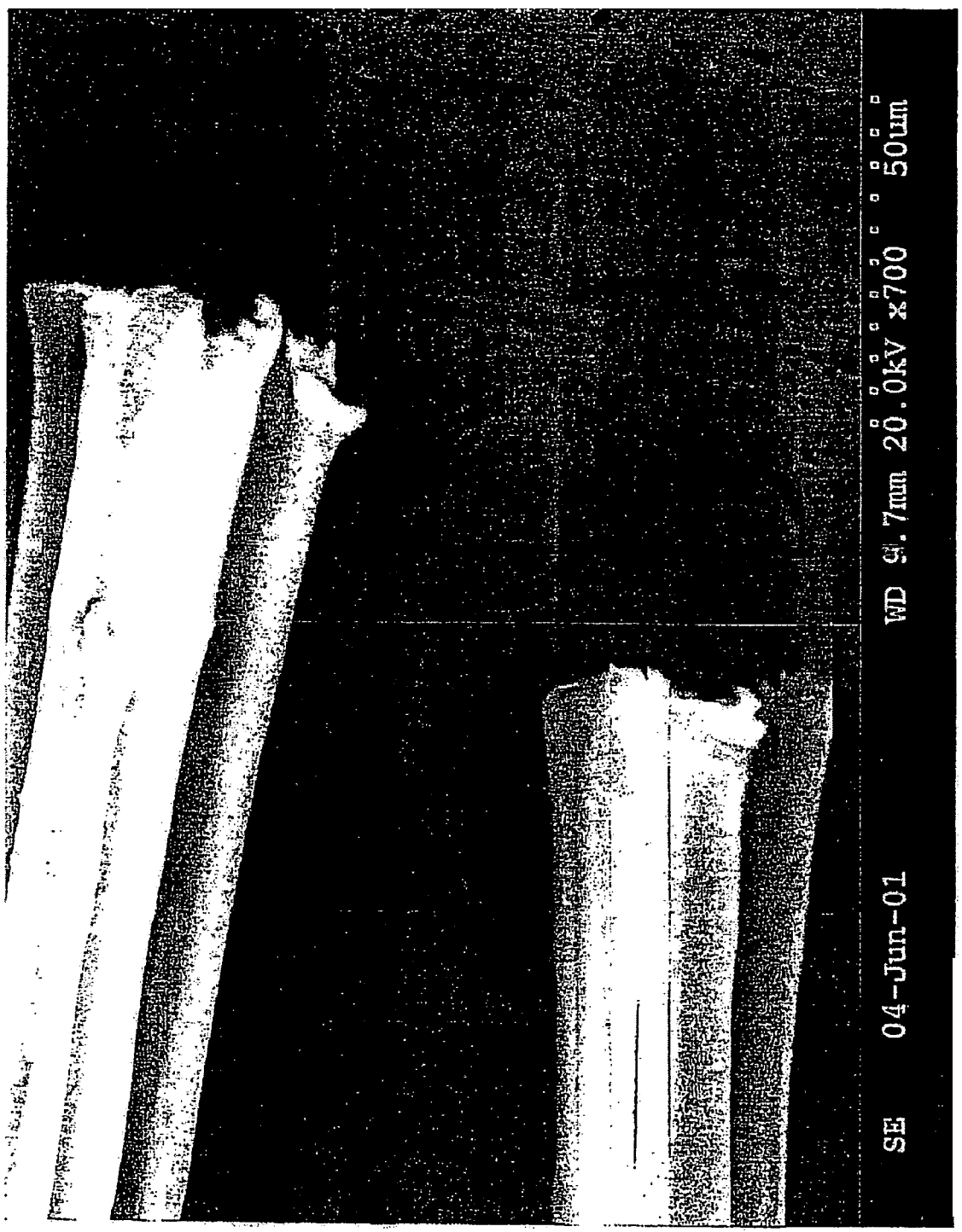
FIG. 2B is a micrograph of enlarged side views of end portions of two channeled polyester fibers such as can be used in a column of a chromatograph.
Figure 3:
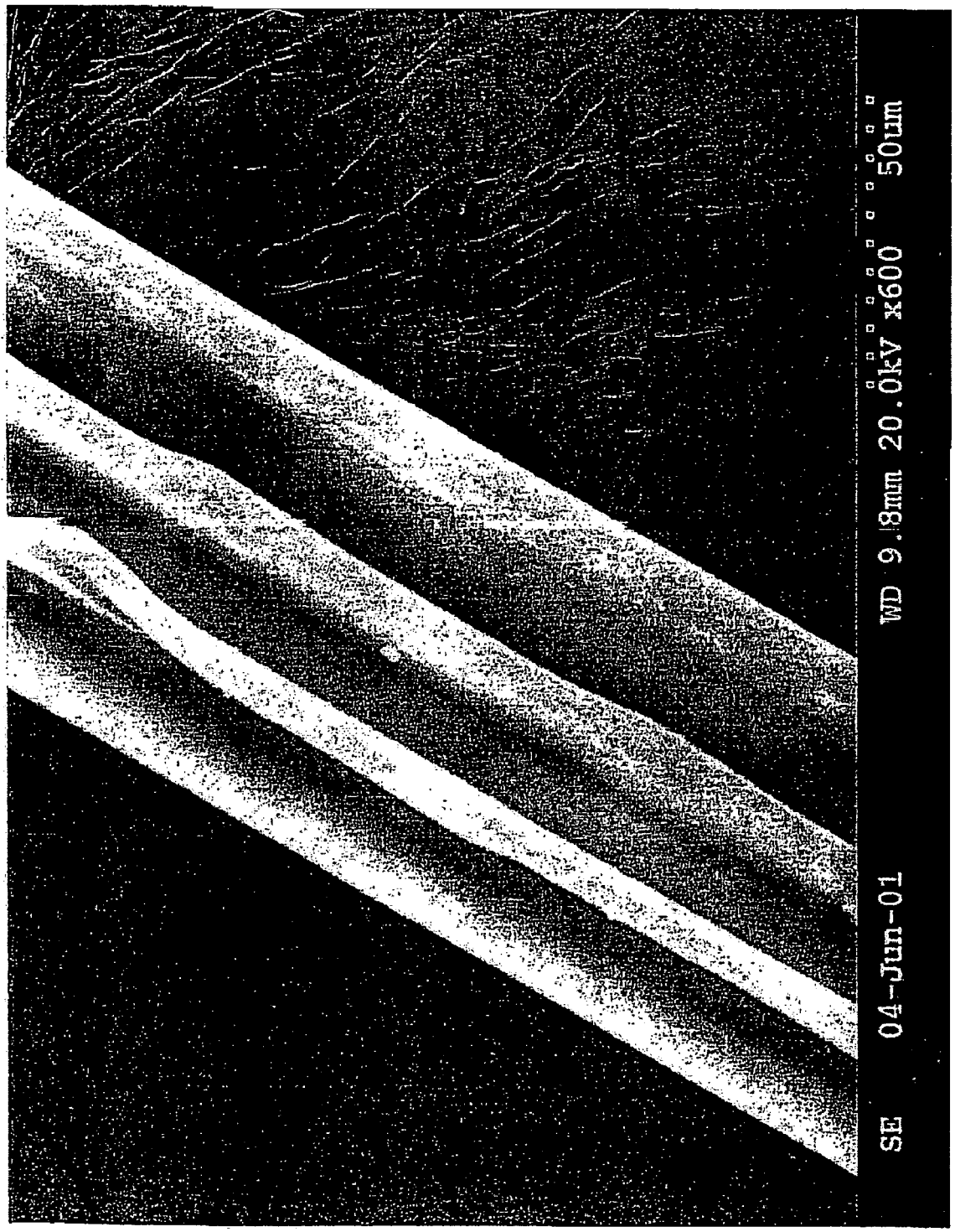
FIG. 3 is a micrograph of an enlarged side view of an intermediate portion of a channeled polypropylene fiber such as can be used in a column of a chromatograph.
Figure 4A:
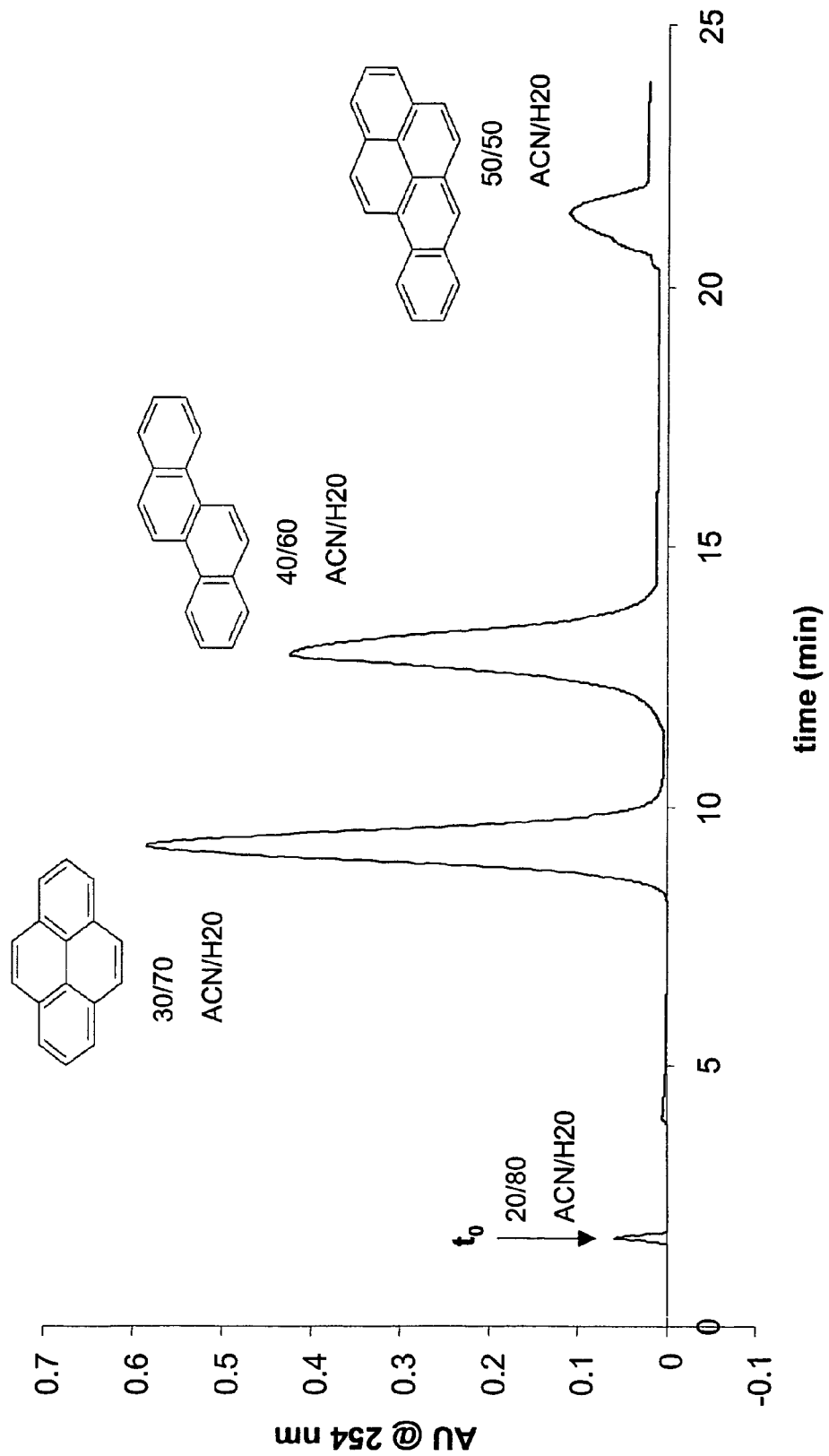
FIG. 4A is a graphical presentation of the time variation of absorbance that is illustrative of the separation of three polyaromatic hydrocarbons (PAH) compounds by a column filled with channeled polypropylene fibers.
Figure 4B:
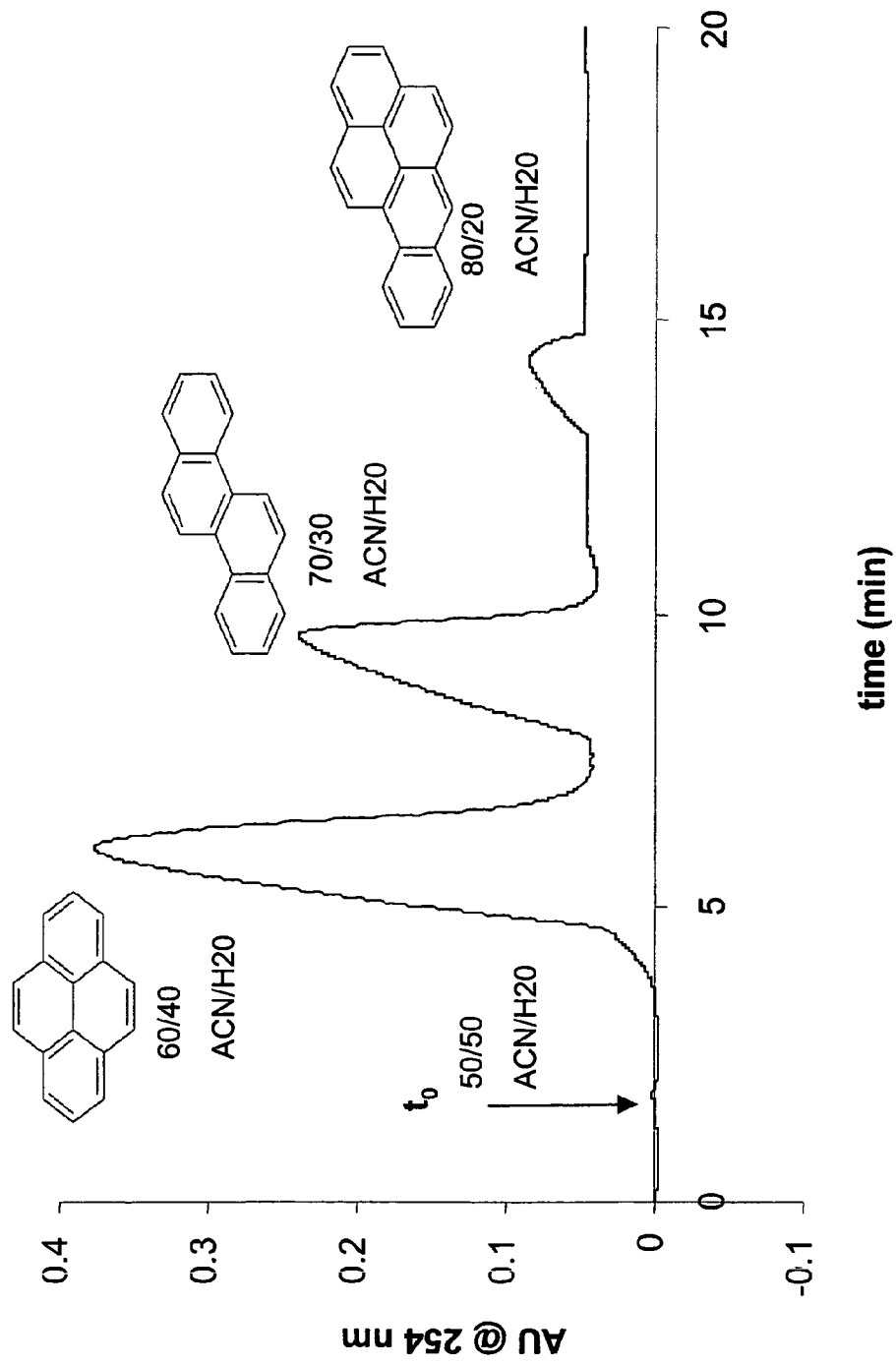
FIG. 4B is a graphical presentation of the time variation of absorbance that is illustrative of the separation of the same three PAH compounds shown in FIG. 4A, but by a column filled with channeled polyester fibers.

FIG. 4A illustrates the separation of three different PAHs on a column filled with channeled polypropylene fibers (such as shown in FIG. 3). Similarly, FIG. 4B illustrates the separation of three PAHs on a column filled with surface-channeled polyester fibers (such as shown in FIGS. 2A and 2B). As noted in FIGS. 4A and 4B, different relative concentrations of acetonitrile (ACN) to water were required to elute the solute species from the stationary phase and to obtain the chromatograms. Thus, gradient elution methods (i.e., changes in solvent composition) may be employed to elute the solute species from the stationary phase and to obtain the chromatograms. This is direct evidence of chemical interactions between the analyte molecules and the polymer fibers; as opposed to a more physical and mechanical "filtering" mechanism of retention of the species on the surfaces of the fibers 20.

Different from the use of channeled polymer fibers 20 for the filtration of particulate matter in liquid and vapor streams, the use of channeled fibers 20 as proposed here is clearly based on chemical interactions between the analyte/solutes and the surfaces of the polymer fibers 20. The fact that solvent gradients are required to separate the compounds as depicted in FIGS. 4A and 4B clearly demonstrates that this is the case. For example, the mixture of PAH's is completely immobilized on the polypropylene surface in aqueous solution to the point where the acetonitrile (ACN) concentration makes up 30% of the solvent composition. The same separation using polyester fibers as the stationary phase requires a 60% ACN to 40% $H_2O$ mixture; proving that the two polymers behave differently.

Liquid chromatography itself is based on the relative distribution between the solid and solution phases, and so relative retention characteristics are an excellent indicator of the actual interactions. The use of different combinations of polymer stationary phases, analyte/solutes, and mobile phases provides empirical insights into the retention processes. In order to obtain more specific thermodynamic information about the attraction of solutes to the fibers, atomic force microscopy (AFM) can be employed to probe the surfaces. In particular, AFM probe tips having different chemical modifications (e.g., polar, hydrophobic, etc.) can be used to study the interactions. The AFM can be used to simply determine the attractive forces under different solvent conditions. However, no imaging of the surfaces is required per se.

Figure 5A:
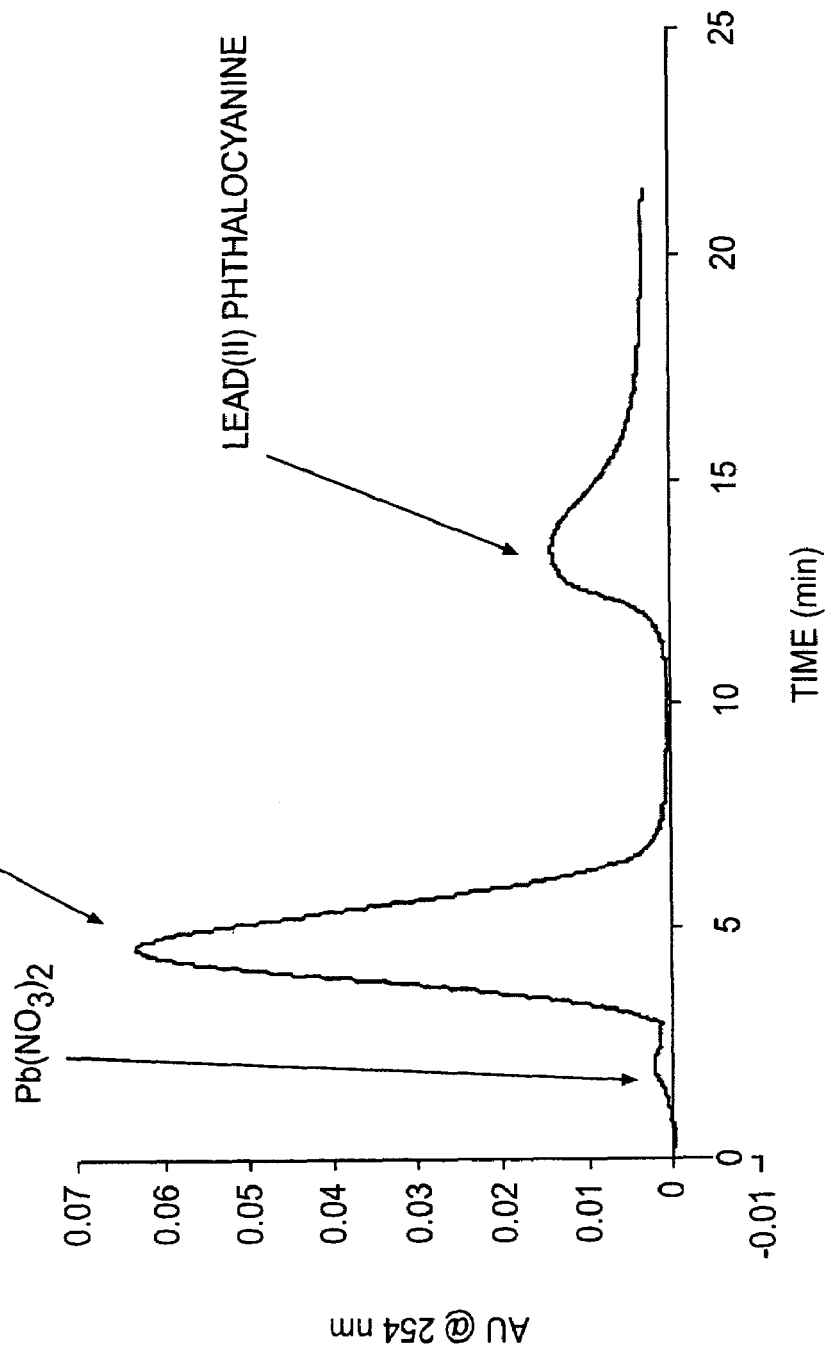
FIG. 5A is a graphical presentation of the time variation of absorbance that is illustrative of the separation of three lead-based compounds by a column filled with channeled polypropylene fibers.
Figure 5B:
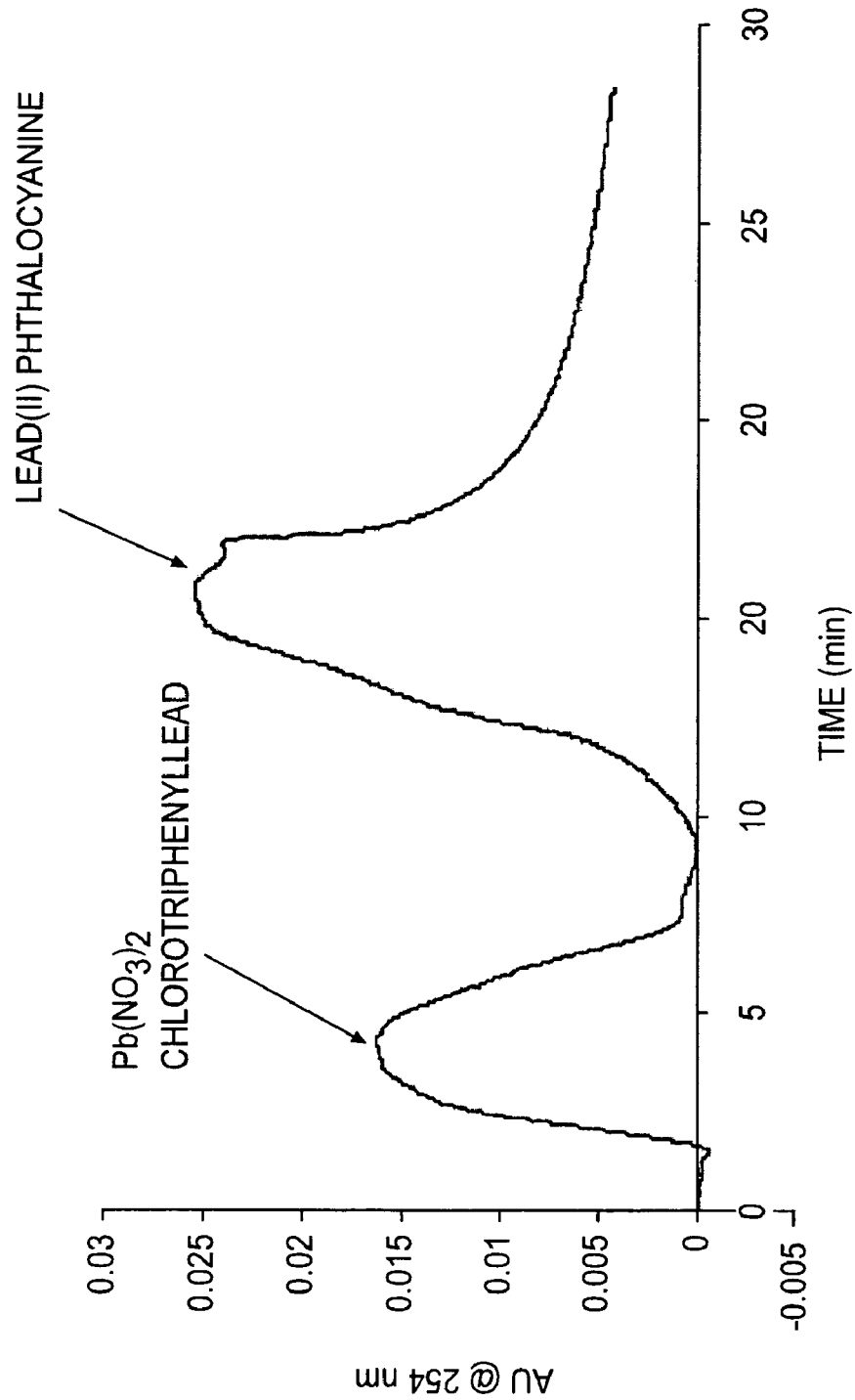
FIG. 5B is a graphical presentation of the time variation of absorbance that is illustrative of the separation of the same three lead-based compounds shown in FIG. 5A, but by a column filled with channeled polyester fibers.
Figure 6:
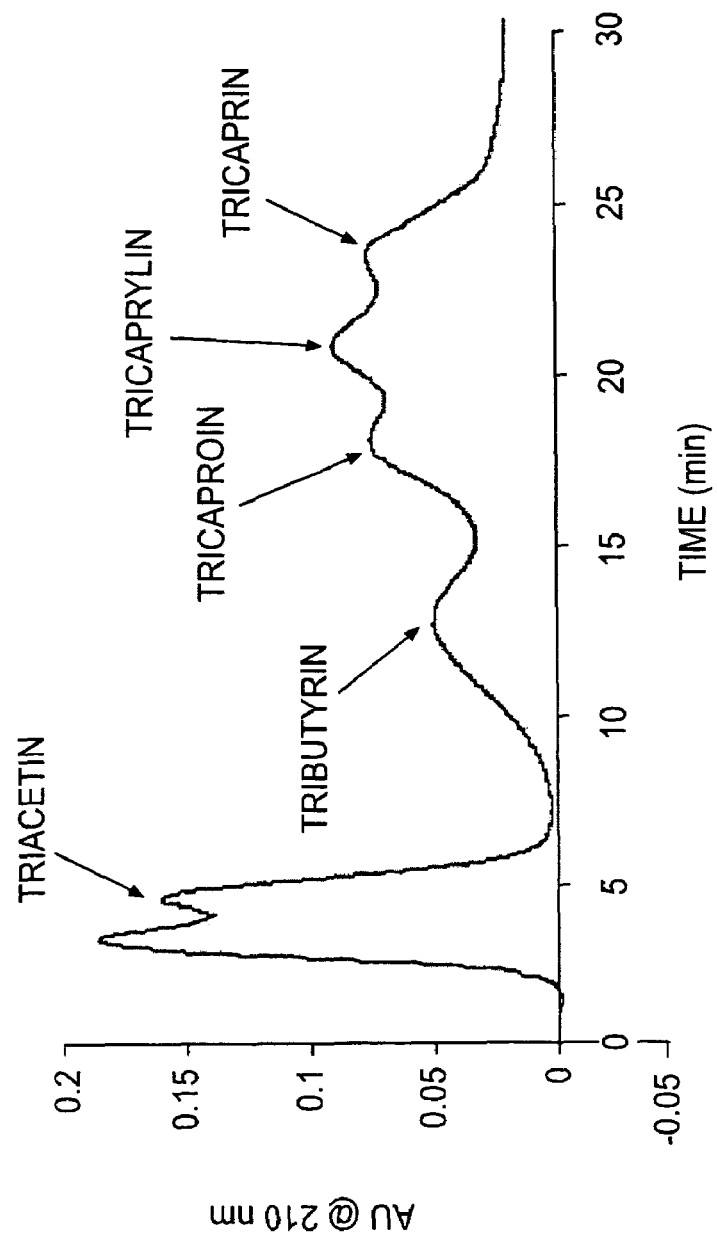
FIG. 6 is a graphical presentation of the time variation of absorbance that is illustrative of the separation of five lipid compounds by a column filled with channeled polyester fibers.

FIG. 5A illustrates the use of a column packed with channeled polypropylene fiber to separate three species of lead-based compounds. Similarly, FIG. 5B illustrates the separation of the species of these same three lead-based compounds using a column packed with channeled polyester fiber. The vertical axis in each of FIGS. 5A and 5B is a measure of the absorbance of light at 254 nanometers by each species. The greater the absorbance of that light, then the higher the number of absorbance units (AU) that is recorded on the chromatogram. The horizontal axis is the time axis that measures how long it takes for the majority of the species (the peak) to be detected by the absorbance of the light at 254 nanometers. Referring to FIG. 5A for example, the chlorotriphenyllead species shows a peak reading of about 0.06 absorbance units (AU's) of light at 254 nanometers at 5 minutes after the 0.02 milliliter volume of solution containing the chlorotriphenyllead species was introduced into the column that was packed with the channeled polypropylene fiber.

FIG. 5A illustrates that the lead nitrate species has less of a strong interaction with the polypropylene fibers in the column than either the chlorotriphenyllead species or the lead (II) phthalocyanine. The lead nitrate peak (though barely above zero) occurs earlier in time than either of the peaks of the chlorotriphenyllead species or the lead (II) phthalocyanine species. Of the three lead-based species tested, the lead nitrate species has the least affinity for the polypropylene fibers in the column. Moreover, the lead nitrate species has a different affinity for the polypropylene fibers in the column because the lead nitrate species has a different chemistry than each of the chlorotriphenyllead species and the lead (II) phthalocyanine species.

Since FIGS. 4A, 4B, 5A, 5B, 6, 7A and 7B are based on absorbance of light at a particular wavelength, the peak height of each species doesn't necessarily reflect the relative concentrations of each of the species because each of them absorbs that wavelength with different strengths.

Figure 7A:
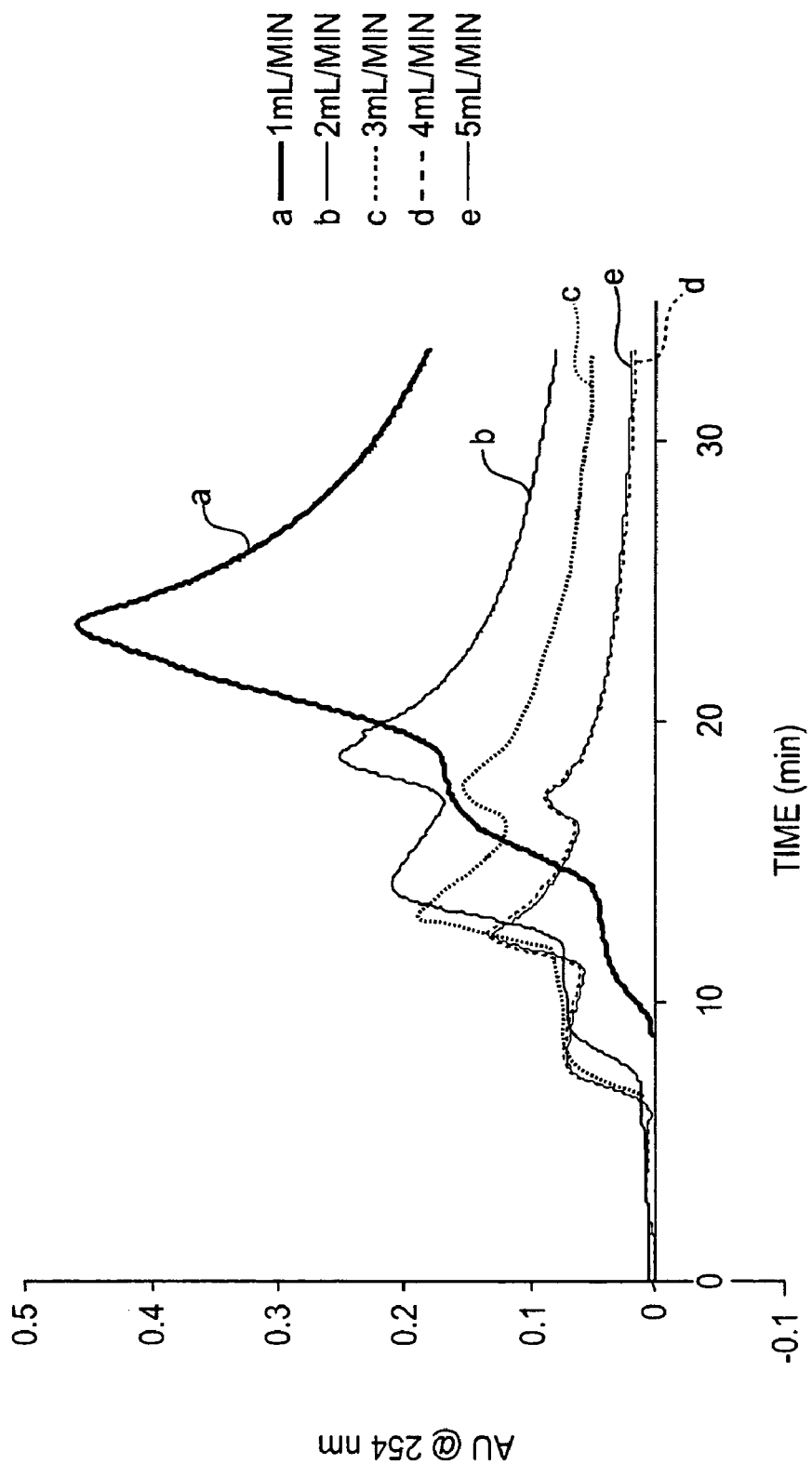
FIG. 7A is a graphical presentation of the time variation of absorbance that is illustrative of the separation of polyaromatic hydrocarbon compounds at different flow rates through a column filled with channeled polyester fibers.
Figure 7B:
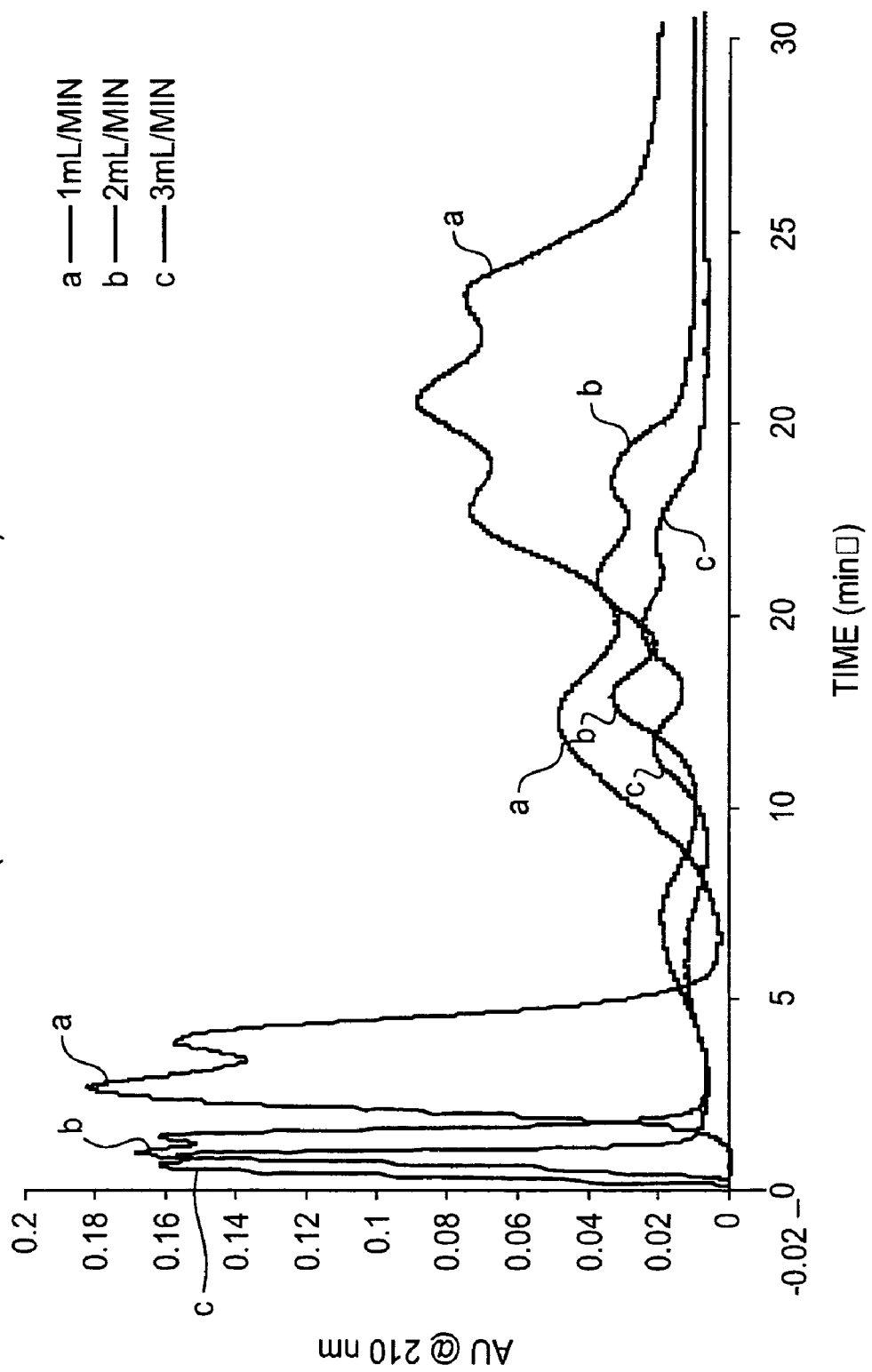
FIG. 7B is a graphical presentation of the time variation of absorbance that is illustrative of the separation of lipid compounds at different flow rates through a column filled with channeled polyester fibers.

FIGS. 7A and 7B demonstrate the role of the rate at which the volume of liquid is pumped through the column 22. In general, some of the peaks for the individual species are bigger at the low flow rates than for the high rates of flow through the column. However, the actual ability to discern one peak from another peak is as good if not better at the high rates of flow through the column than at the low flow rates. This latter finding concerning resolution of the individual peaks is counter to that observed with conventional column structures. Thus, the columns of the present invention do not necessarily exhibit degradation of the resolution of the chromatograms at the higher flow rates among those that were tested.

The surface-channeled polymer fibers 20 lend themselves to use in a variety of separation methods. In one embodiment, a bundle composed of a plurality of surface-channeled polymer fibers 20 can be disposed with a first set of the ends of the fibers 20 inserted into a first source of a fluid containing at least one species. The second ends of the fibers 20 (the ends opposite the first ends) can be disposed at a remote location that is apart from the location of the first source of fluid. The capillary action of the channels 24 will then transport the fluid from the source to the remote location at which point the transported fluid can be collected in a collection device, e.g., a beaker, a vile, a vat, or any container suitable to the specific process. During the course of the transport, some of the species will attach to the surfaces of the fibers 20. The species that attach to the surfaces of the fibers 20 are removed from the fluid that reaches the remote location. Accordingly, the concentration of the species at the second location becomes reduced as a result of separation of the species from the fluid by chemical attachment of the species to the surface-channeled polymer fibers 20.

In another embodiment, a bundle composed of a plurality of surface-channeled polymer fibers 20 can be dipped into a fluid containing at least one species. Capillary action will draw a portion of the fluid into the channels 24. During the duration of the immersion of the fibers 20 in the fluid, some of the species will attach to the surfaces of the fibers 20. The concentration of the species in the portion of the fluid that has been drawn into the channels 24 and collected in a collection device becomes reduced as a result of separation of the species from that portion of the fluid by chemical attachment of the species to the polymer fibers 20. After a predetermined duration of immersion, the fibers 20 can be withdrawn from the fluid. The species that remain attached to the surfaces of the fibers 20 are thus removed from the fluid. Accordingly, the concentration of the species that remains in the fluid becomes reduced as a result of separation of the species from the fluid by chemical attachment of the species to the surface-channeled polymer fibers 20.

It may be possible to use a single fiber in a micro-scale separation according to one embodiment of the present invention. Such as, for example, in a lab-on-a-chip separation process. In such micro-scale processes, fluid movement could be achieved by, for example, capillary, hydro-dynamic or electro-osmosis means.

Studies are proposed to further evaluate the potential of using channeled polymer fibers in analytical and prep-scale separations. The actual experimental procedure will involve a three-prong approach including: 1) development of column packing methodology, 2) use of atomic force microscopy to study the chemical basis of chemical specificity, and 3) investigations into on-column derivatization of the base polymer fibers.

The preliminary studies involve manual packing of the polymer fibers into the tubing columns 22 as depicted schematically in FIG. 1. The tubing material can be any suitable material. In one embodiment, it can be a metallic tubing, such as steel, though any other suitable tubing material can be utilized including glass, ceramic, or polymeric materials. As shown in FIG. 1A, the illustrated columns 22 have appreciable amounts of dead volume along the flow axis. The quality of any subsequent chemical separation can depend at least in part on the uniformity of the packing of the stationary phase (fibers 20) in the column 22 with regards to dead volume, i.e., where turbulence can occur and molecule-surface interactions are absent.

High quality, reproducible columns 22 are required to adequately study the underlying mechanisms of retention. For instance, in one embodiment, radial compression technologies can be employed to effect more uniform packing of the fibers 20. For example, radial compression can be applied to pack the fibers through utilization of water pressure, heat shrinking technologies, mechanical compression techniques, e.g., mechanical drawing or extrusion processes or any other radial compression method as is generally known in the art. For instance, in one embodiment, the column can be surrounded with tubing formed of polyethylene (PE), and the resulting wrapped column 22 then can be surrounded by a water jacket. Increases in pressure applied to the jacket can squeeze the polyethylene column 22 and thus compress the fibers 20 into a tighter bundle. Chemical separations of model compound classes can be performed to assess the role of compression on the retention qualities of the different fibers. Particular attention can be paid to the trade-offs between packing density, the obtained resolution, and the backpressure required to provide the desired flow through the column 22.

In one embodiment, the present invention is directed to monolithic cartridges that can be utilized as a stationary phase in liquid separations. In particular, the monolithic cartridges include capillaries between adjacent fibers that can provide bulk wicking action in the disclosed cartridges. For purposes of this disclosure, the term 'monolithic' is herein defined to refer to a component formed of a plurality of units (i.e., two or more units) acting as a single, substantially rigid, uniform whole.

In one embodiment, the monolithic cartridges of the present invention can include nominally aligned fibers that have been bonded, pressed, or fused together at one or more locations along the fiber length. For example, in one embodiment, the monolithic cartridge can include two adjacent fibers that can be bonded along the entire length of one of the fibers. In another embodiment, two adjacent fibers in the cartridge can be bonded at a single site along their lengths, for instance merely a spot bonding between the fibers where they briefly contact one another. Similarly, two fibers can be bonded, pressed, or fused to each other at multiple spaced locations along their lengths. Moreover, while the monolithic cartridges of the present invention can include individual fibers bonded, pressed, or fused to one another, it should be understood that it is not a requirement of the invention that all of the fibers within the monolithic cartridges be bonded, pressed, or fused to another. The disclosed monolithic cartridges can include fibers that are not bonded to another. The monolithic cartridges of the present invention require only suitable inter-fiber interaction such that the cartridge is monolithic as herein defined, that is, such that the fiber bundle acts as a single, substantially rigid, uniform whole and exhibits bulk wicking action.

Among other advantages, bonding, pressing, or fusing polymeric fibers together within the fiber bundle can form capillaries between adjacent fibers so as to provide the bulk capillarity to the cartridges of the present invention. In addition, physical interaction among fibers can help to prevent the formation of dead volume within the column, as well as improve molecule/surface interaction along the length of the cartridge.

In one embodiment, the monolithic cartridges of the present invention can include surface-channeled fibers such as those described above. According to this embodiment, the monolithic cartridge can exhibit both micro-level capillarity due to the wicking capabilities of the individual channels along each fiber length as well as macro-level capillarity between adjacent fibers of the monolithic cartridge. In addition, monolithic cartridges including surface-channeled fibers can exhibit very high surface area for interaction between the stationary phase and the liquid phase during separation processes.

The monolithic cartridges of the present invention are not limited to those formed of capillary-channeled fibers, however. In one embodiment, fibers having a substantially circular cross-section can be used to form the disclosed cartridges. For example, in one embodiment, a fiber bundle of circular fibers can be physically or chemically bonded together at spaced locations throughout the bundle to form a monolithic cartridge that can exhibit bulk wicking action through the capillaries between adjacent fibers.

Figure 8:
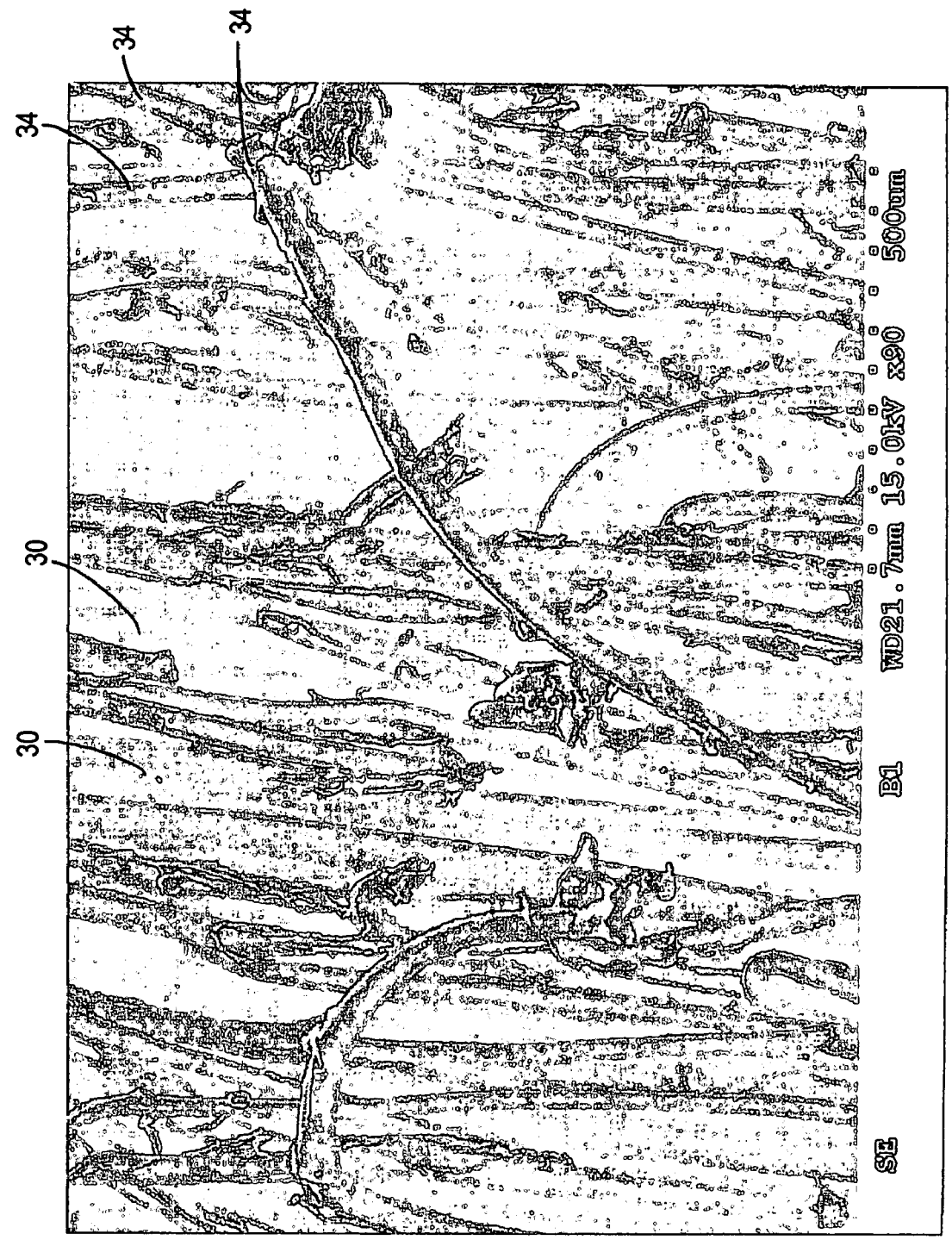
FIG. 8 is a scanning electron micrograph of a portion of a monolithic cartridge of the present invention.

FIG. 8 is a scanning electron micrograph of a monolithic cartridge according to the present invention including a plurality of nylon fibers having nominally circular cross-sections. As can be seen, the fibers within the bundle are nominally aligned with one another. In addition, the bundle includes random points or lengths of bonding 30 between adjacent fibers 34.

Figure 9:
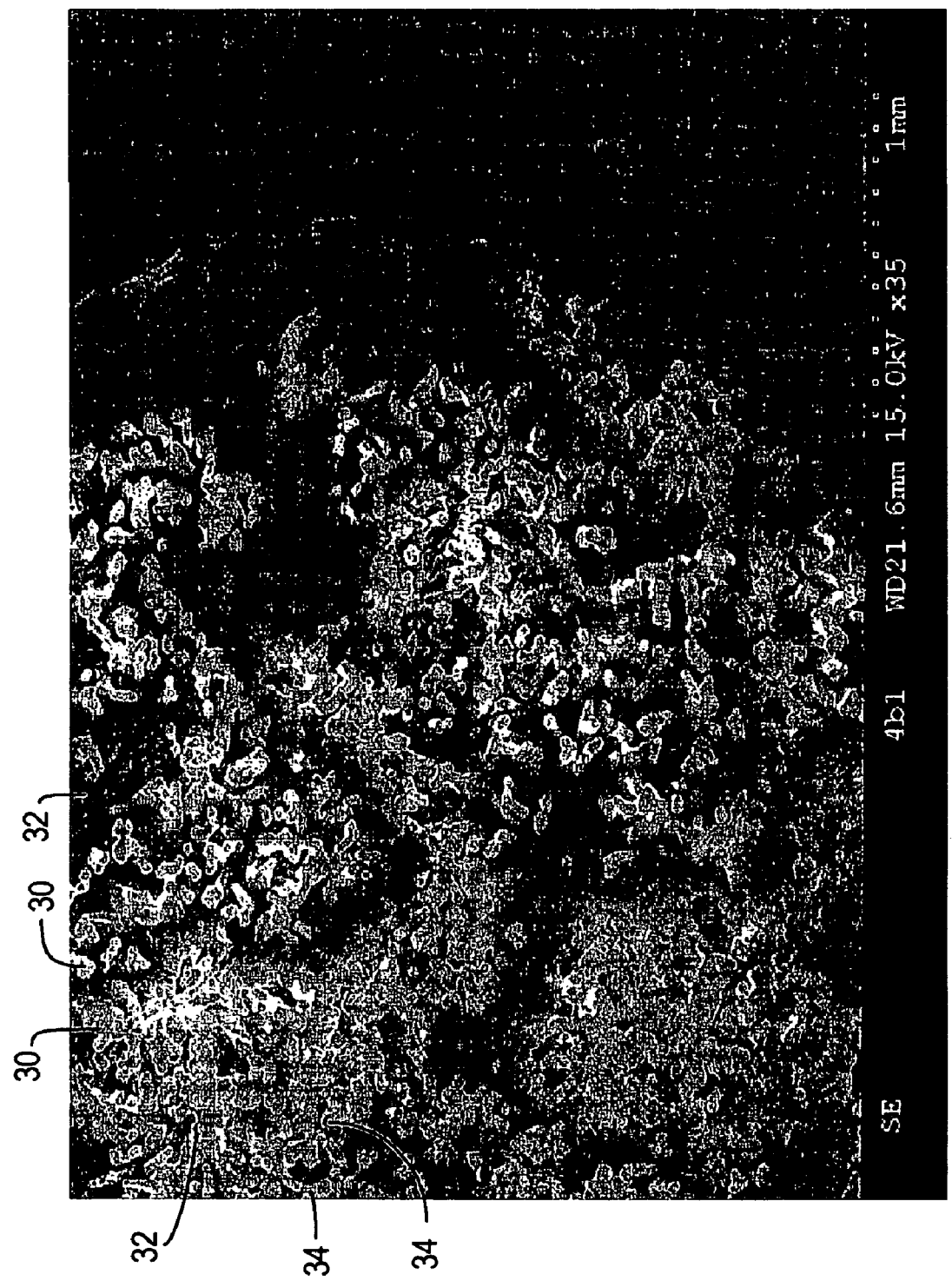
FIG. 9 is a scanning electron micrograph illustrating the cross section of a monolithic cartridge of the present invention.

FIG. 9 is a scanning electron micrograph of a similar monolithic cartridge formed of polyester fibers and shown in cross-section. The figure shows the regions of porosity 32 between individual fibers 34, which provide the bulk or macro-level capillarity to the cartridge. The random points of bonding 30 between individual fibers can also be seen in FIG. 9.

In general, any suitable method that promotes the formation of the fiber bundle as a single, substantially rigid, uniform whole cartridge while defining capillaries between individual fibers to provide bulk wicking action to the cartridge can be utilized. For instance, the individual fibers of a monolithic cartridge can be bound one to another with either physical or chemical bonds. Moreover, the preferred method for bonding, pressing, or fusing adjacent fibers within any particular cartridge can generally vary depending primarily on the fiber material.

For example, in some embodiments, individual fibers can be formed of a thermoplastic polymer such as polyester or polypropylene that is amenable to melt-spinning formation processes. According to one embodiment, following formation of such individual fibers, a plurality of the fibers can be heat bonded to form the monolithic cartridges of the invention. For instance, a plurality of fibers can be passed through a steam chest or heating cabinet and brought to a temperature at or above the softening temperature of the fiber material in order to physically heat bond adjacent fibers to one another at points of contact along the fibers. Particular examples of processes that can be utilized for forming bonded fiber bundles such as those of the present invention are further described in U.S. Pat. No. 4,996,107 to Raynolds, et al. and U.S. Pat. No. 6,616,723 to Berger, both of which are incorporated herein by reference.

In other embodiments, bonding agents can be utilized in forming the disclosed cartridges. For example, in one embodiment, at least some of the fibers contained in the cartridges can include a bondable material either integral to or topical to the fibers. Following any necessary activation of the bondable material, the fibers including the bondable material can bind to adjacent fibers at points of contact within the fiber bundle, leaving capillaries between the fibers and throughout the length of the fiber bundle. Bondable materials can include, for example, cross-linking agents applied to the individual fibers or functional moieties included on some or all of the polymers forming the fibers.

In some embodiments of the present invention, the monolithic cartridge can include a wrap that can surround the fibers and disposed along the axial length of the fibers. According to this particular embodiment, actual physical or chemical bonding or fusion of the fibers within the cartridge may not be necessary, as the wrap material encasing the fibers can provide suitable pressure to the individual fibers within the cartridge so as to press adjacent fibers together and form the wicking capillaries between the adjacent fibers. According to this particular embodiment, wherein adjacent fibers are not necessarily fused together so as to form the disclosed wicking capillaries, the fibers can be considered to be pressure bonded. Of course, the term "pressure bonded" can also encompass embodiments wherein the pressure applied to the cartridge does lead to actual fusion of adjacent fibers. In addition, the presence of the wrap material around the fibers can provide the rigidity and unifying wholeness to the component parts of the monolithic structure without the necessity of forming physical or chemical bonds within the fibers.

Figure 13:
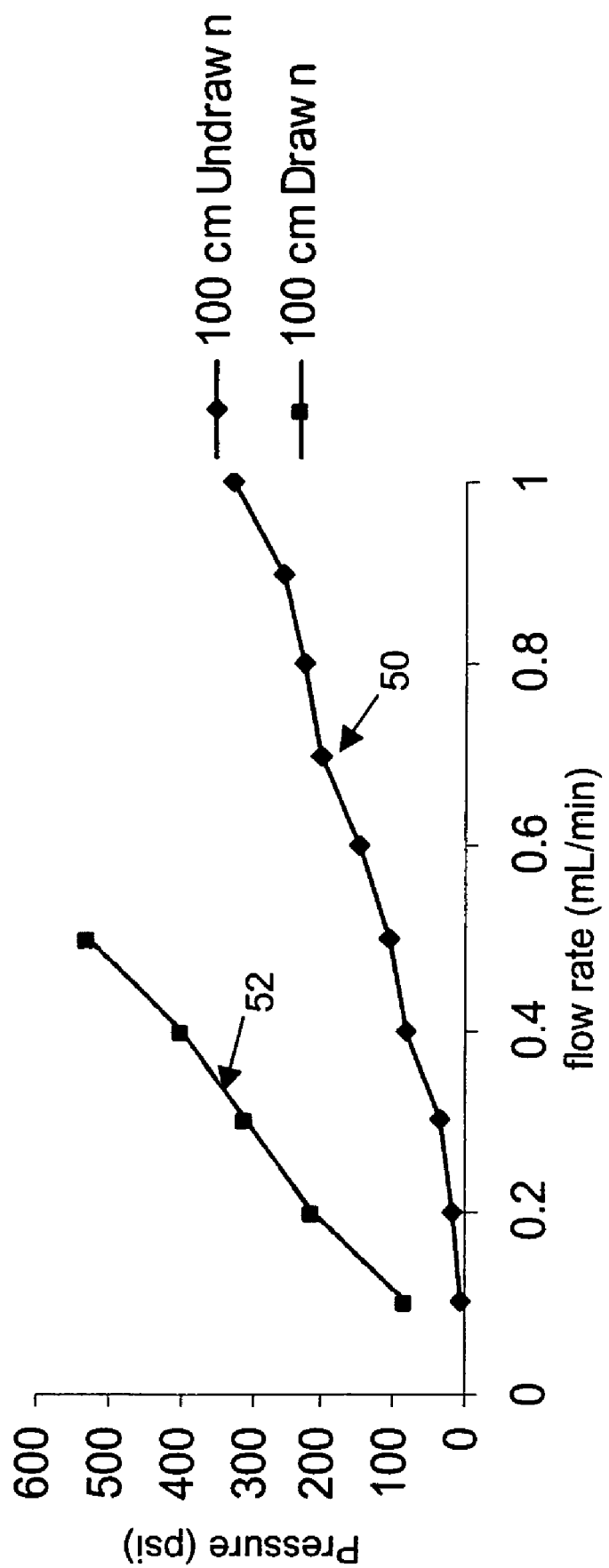
FIG. 13 graphically compares backpressures at various flow rates for a column before and after the application of radial compression to the column.

For example, according to one embodiment, the fiber bundle of the cartridge can be encased in a polymeric wrapping material along the axial length of the fibers and radial compression can be applied to the cartridge by any suitable means. Upon application of radial compression, the radial dimension of the cartridge can decrease as the fibers are pressed together and the wicking capillaries form between fibers. Thus, a bulk wicking capillary network can develop in the cartridge between the adjacent fibers. Referring to FIG. 13, backpressure vs. flow rate data is illustrated for a column comprising a plurality of surface-channeled polymer fibers before (at 50) and after (at 52) the application of radial compression to the column. More specifically, a column of surface-channeled polypropylene fibers wrapped with a polymeric outerwrap was formed. The column (100× 0.13 cm i.d.) was then drawn through an orifice to compress the column wall. As can be seen, following compression, the backpressure of the column (now 100×0.10 cm i.d.) has increased over the undrawn column at identical flow rate, due to the decrease in void fractions between the adjacent fibers within the column.

In one embodiment, the monolithic cartridges of the invention can include a nonporous wrap encasing the cartridge along the axial length of the fibers. For instance, when considering standard liquid chromatography systems and techniques, in which liquid is pumped or otherwise forced through the bundle, the monolithic cartridge can be encased in a nonporous wrap such as a suitable metallic or polymeric wrap material.

In other embodiments, the monolithic cartridges of the invention do not require a nonporous wrap. For example, in those embodiments in which liquid moves across the cartridge via capillary action alone, e.g., lateral flow assay applications or thin layer chromatography systems, the plurality of fibers can include physical and/or chemical bonds between the fibers to form the wicking capillaries and the cartridge need not include an outer wrap material at all. Optionally, in another embodiment, the cartridge can include a wrap of a porous material surrounding the length of the fibers to provide uniformity and rigidity to the monolithic structure, and, in some embodiments, providing pressure bonding between the fibers.

Figure 10:
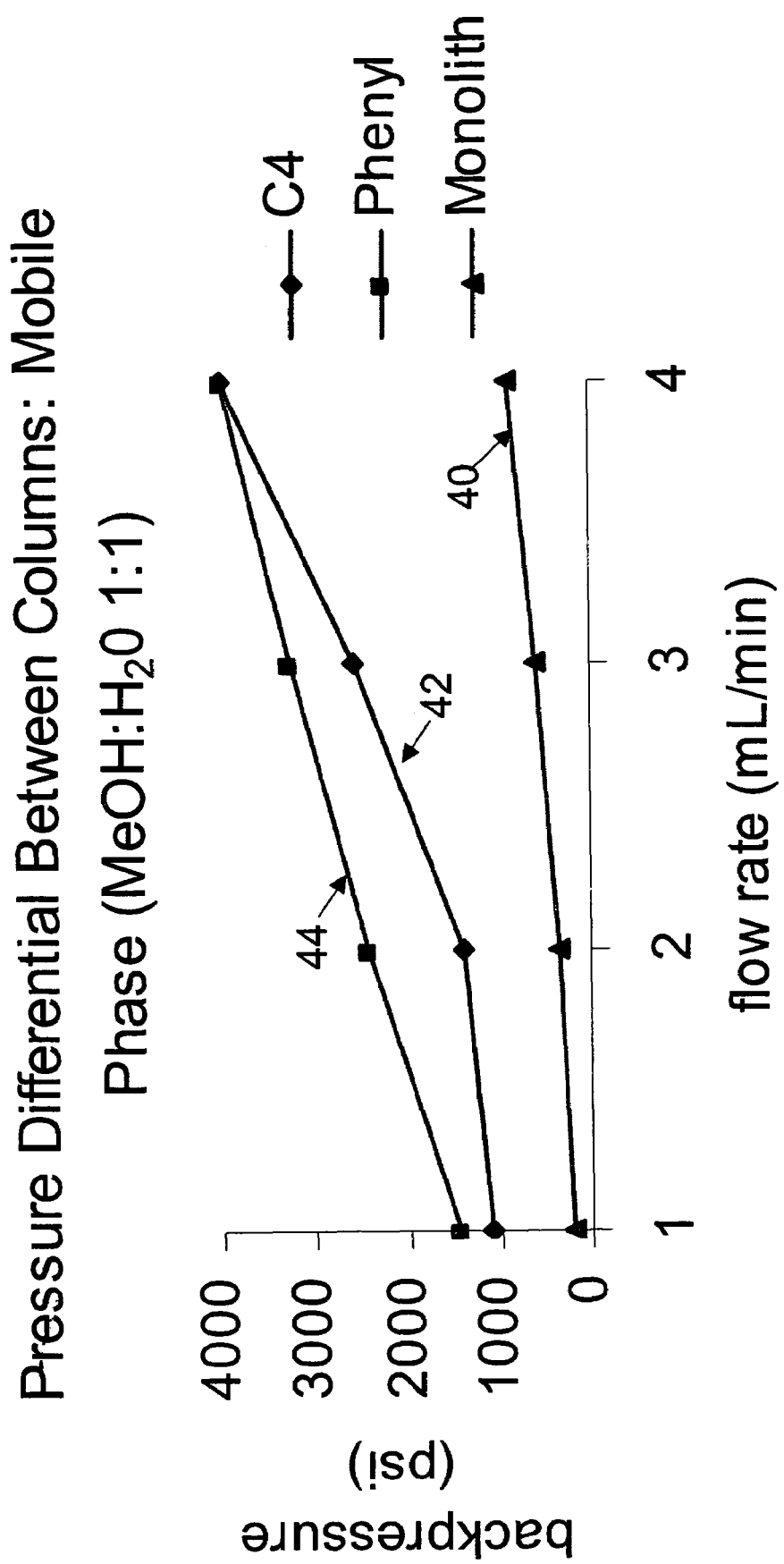
FIG. 10 graphically compares the effect of volume flow rate on resulting backpressure of three separation columns including various stationary phases.

The monolithic cartridges of the present invention can not only exhibit good bulk capillarity, allowing relatively high volume flow rates through the cartridges, but can do so at lower backpressures than those attainable for previously known packed particular separation columns. Moreover, in those embodiments wherein the monolithic cartridge includes surface-channeled polymer fibers, the micro-level wicking properties of the individual fibers can add to the bulk wicking properties of the cartridge as well as providing higher surface area per unit volume and thus can further improve mass transfer and separation characteristics of the disclosed systems. As such, standard liquid chromatography columns utilizing the disclosed monolithic cartridges can be operated lower instrumentation overhead, which can translate to lower operational costs. For example, referring to FIG. 10, backpressure was graphed at various flow rates for a column of 4.6 mm inner diameter and 305 mm in length utilizing three different stationary phases. As can be seen, backpressures obtained for the monolithic cartridges of the present invention, shown at 40, are considerably lower than those for a commercial $C_4$-derivatized silica packed-particulate column, shown at 42, as well as for a commercially available phenyl-derivatized packed particulate column, shown at 44. For instance, in one embodiment of the present invention, separation processes can be run at flow rates up to about 6 mL/min at backpressures of less than about 1200 psi.

In one embodiment, the monolithic cartridges of the present invention can be fairly rigid structures (i.e., capable of sustaining the overall shape of the structure under normal processing and handling conditions). This can greatly simplify handling and processing of the disclosed materials. In addition, the disclosed monolithic cartridges can be formed into any desired size and shape. For example, the monolithic cartridges can be manufactured with any predetermined dimensionality and utilized in existing chromatographic systems by merely mounting the monolithic cartridge in place of the conventional chromatographic column of the system.

Future investigation of the disclosed devices and methods will seek to take the basic chemical principles governing packing density and the chemical basis of chemical specificity and begin to tailor the surfaces of the polymer fibers in such a way as to have specificity for particular classes of chemical compounds. The preliminary studies have demonstrated that polyester and polypropylene fibers have different surface chemistries, though each nominally has what is termed reversed-phase character. That is to say that each has a propensity to bind non-polar molecules. As mentioned previously, a number of other base polymers could be fabricated as disclosed to gain access to other degrees of chemical specificity.

Additionally, the surfaces of the polymer fibers could be modified, while maintaining the high surface area-to-volume ratio and the basic structure. Applications in analytical separations for a wide range of compound classes are anticipated by changing the identity of the base fiber or performing chemical derivatization of the surfaces of the fibers. At least portions of the surfaces of the polymer fibers can be modified to a predetermined chemical reactivity. For example, the predetermined chemical reactivity could be obtained by modifying at least portions of the surfaces of the polymer fibers to a predetermined level of hydrophobicity. Thus, active sites on the fiber surfaces could be functionalized to gain more or less hydrophobic character. The predetermined chemical reactivity also could be obtained by modifying at least portions of the surfaces of the polymer fibers to a predetermined ionic character. For example, the surfaces of fibers formed from polyvinyl alcohol (PVA) might be protonated in situ by an acidic mobile phase to produce an ion exchange column.

High performance liquid chromatography will be used as the first-level screening tool in the characterization. This work will not only focus on chemical separations, but also on the capacity to retain on-column target waste species of relevance to a wide range of industries (i.e., how much solute can be immobilized in a fiber 'cartridge'?). This latter aspect is the most relevant characteristic in terms of using these fiber-types in waste stream treatment strategies.

The disclosed invention can be further understood with reference to the following Examples.

EXAMPLE 1

Channeled propylene fibers having nominal diameters of approximately 50 μm and 8 branched channels running along their length were examined for protein separations. The channeled fibers were obtained from Eastman Chemical, Kingsport, Tenn. from a bobbin of fibers measuring more than 1000 meters in length.

Bundles of approximately 1200 fibers were loaded co-linearly into 4.6 mm i.d., 306 mm long stainless steel tubing (available from Valco Instruments, Houston, Tex.). Bundles were passed through the column such that the general alignment of the fibers within the column was longitudinally parallel such that broadening due to eddy diffusion, i.e., tortuous paths, was expected to be minimal.

The fiber lengths were trimmed to be flush with the tubing ends, and the column ends were sealed with 0.75 mm thick, 6.35 mm diameter frits including 10 μm pores and completed with column end fittings (available from Valco Instruments). Each fiber column had a packing mass of about 1.7 grams. Column porosity determinations for the polypropylene fiber columns yielded values of approximately 0.66. The columns were flushed repeatedly with organic solvent (methanol and acetonitrile) and distilled water.

The chromatographic system consisted of a Waters (Milford Mass.) Model 600S HPLC pump with a 6 port Rheodyne injection valve (Rohnert Park, Calif.) fitted with a 10 μL injection loop. The prepared columns were mounted in place of conventional columns in the system. A Waters 2487 dual wavelength absorbance detector was employed at 216 nm, and the separations were performed at a solvent flow rate of 1.5 mL/min.

HPLC-grade water (Fisher Scientific, Pittsburgh, Pa.) was used for the preparation of the protein solutions. Each protein stock solution was prepared as a 1 ppm solution using 5:95 (ACN-water) containing 0.1% TFA. The four proteins and the TFA used in the mobile phase were purchased from Sigma Aldrich (Milwaukee, Wis.). Particular proteins were superoxidase (SOD) from bovine erythrocytes (EC No. 232-943-0), myoglobin from horse skeleton muscle (EC No. 309-705-0), hemocyanin from human, and hemoglobin from horseshoe crab. The mobile phase was prepared from HPLC-grade ACN, water, and 2-propanol. The protein test solutions were stored at 6° C.

The protein test mixture was prepared by mixing 2 mL of each protein stock solution in a 20 mL vial. The column was rinsed with mobile phase 95:5 water and (1:1) propanol-acetonitrile for 10 minutes before each injection. The separation was achieved using a gradient elution of 95:5 to 35:65 water containing 0.1% TFA (v/v)-propanol/ACN (1:1) (containing 0.085% TFA) over 70 minutes at 1.5 mL/min.

Figure 11:
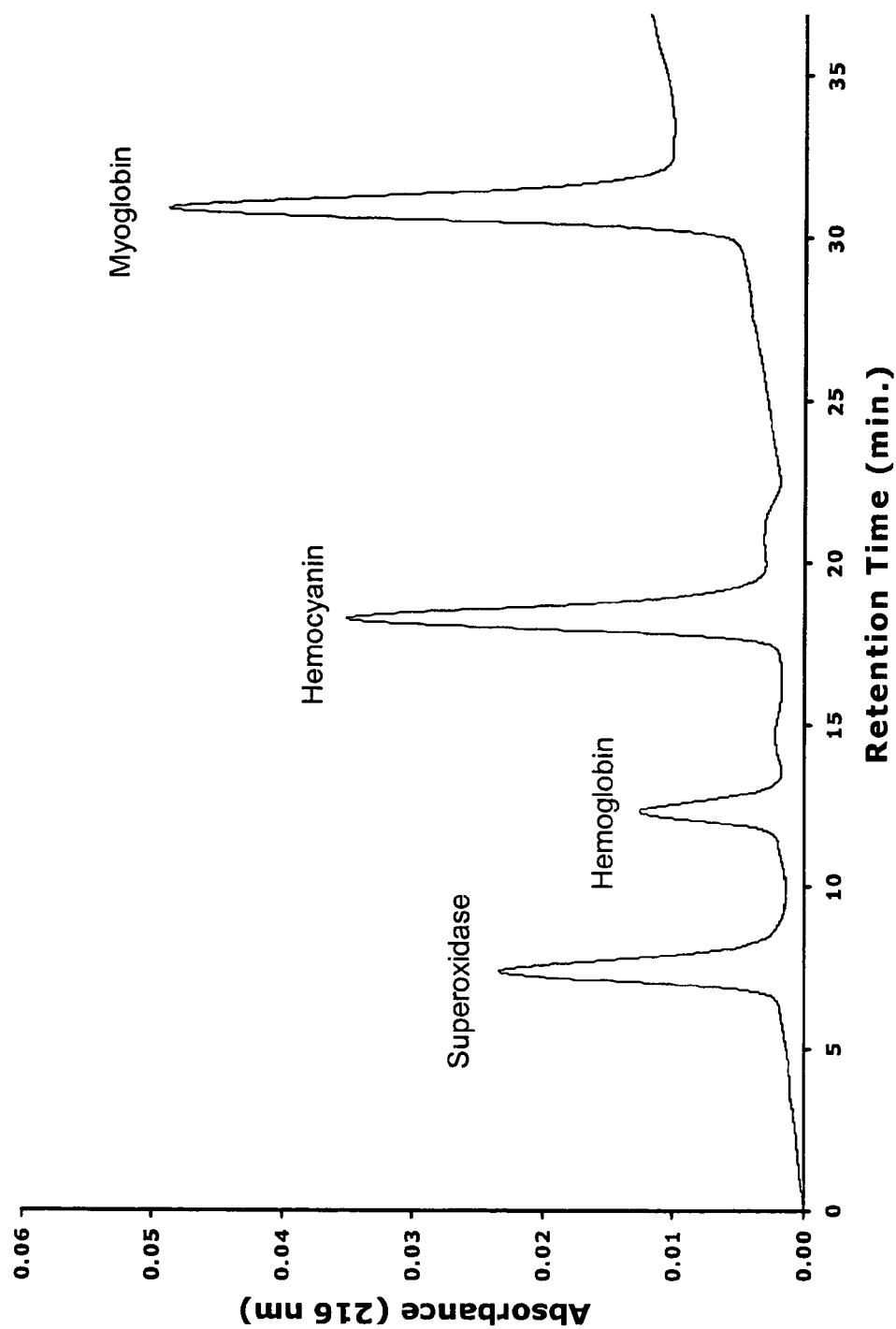
FIG. 11 illustrates the separation of a mixture of proteins utilizing a separation column comprising surface-channeled polymer fibers as described herein.

The gradient elution chromatogram of the mixture is shown in FIG. 11. Table 1, below, summarizes the basic characteristics for the separation. As seen in the Figure, each of the peaks is very well resolved and quite symmetric in profile and the elution order does not correspond to the analyte molecular weights (31.2, 60, 75, and 17 kDa, respectively).

TABLE 1

| Protein | Retention Time | Retention Factor | Selectivity Factor | Peak half-width | Resolution | Asymmetry | PC |
|---|---|---|---|---|---|---|---|
| SOD | 7.5 | 2.3 | — | 0.95 | — | 1.4 | 4.6 |
| Hemoglobin | 12.4 | 4.4 | 1.9 | 0.86 | 1.4 | 1.09 | 8.5 |
| Hemocyanin | 18.3 | 6.9 | 1.6 | 0.85 | 1.6 | 1.08 | 13 |
| Myoglobin | 31 | 12.5 | 1.8 | 0.99 | 2.9 | 1.05 | 18 |

EXAMPLE 2

Figure 12:
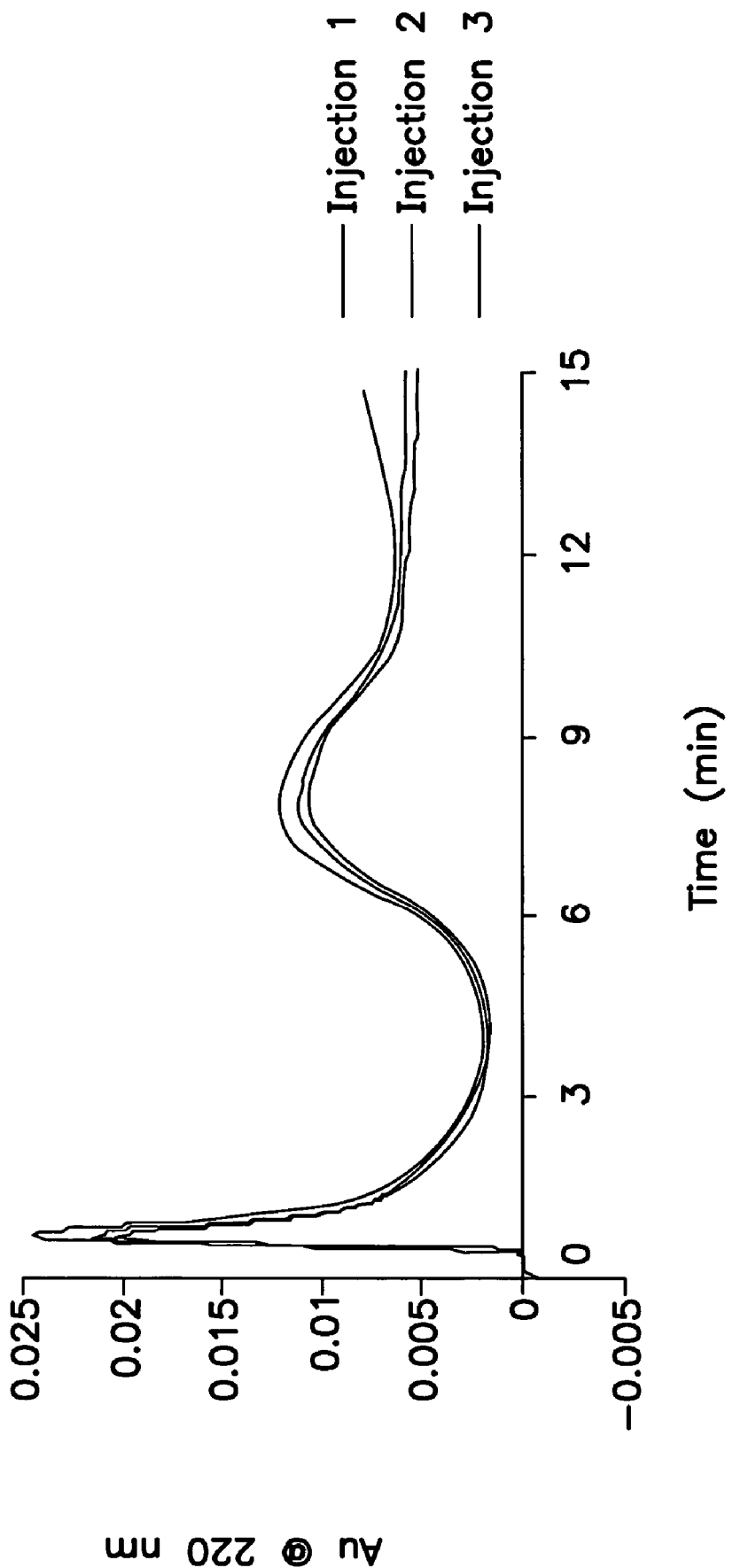
FIG. 12 illustrates the separation of a mixture of proteins utilizing a monolithic cartridge of the present invention.

A monolithic cartridge of heat-bonded polyester fibers having substantially circular cross-sections was utilized to selectively separate solutions including the proteins ribonuclease A and cytochrome C. The solvent gradient was varied from 80:20 (water (0.1% TFA):acetonitrile(0.06% TFA)) to 70:30 over 10 minutes at a liquid volume flow rate of 1.75 mL/min. Systems and methods used for the separations were similar to those described in Example 1, above. Three separations of 20 μL injections were performed. Results of the separations are graphically illustrated in FIG. 12. As can be seen, the three injections yielded very reproducible separations.

While a preferred embodiment of the invention has been described using specific terms, such description is for illustrative purposes only, and it is to be understood that changes and variations may be made without departing from the spirit or scope of the following claims.

What is claimed is:

1. A liquid chromatography device comprising a monolithic cartridge having a first end and a second end, the monolithic cartridge including a plurality of nominally aligned polymeric fibers, the monolithic cartridge including a nonporous wrap surrounding the plurality of fibers and disposed along the axial length of the nominally aligned fibers from the first end to the second end, wherein the polymeric fibers are the stationary phase of the liquid chromatography device and exhibit a chemical affinity for a component of a liquid phase, at least a portion of the fibers being directly fused to one another at points of contact along the fiber lengths such that the monolithic cartridge includes spot bonds located randomly throughout the entire length of the monolithic cartridge, the monolithic cartridge defining a plurality of capillaries capable of bulk wicking the liquid phase between adjacent fibers from said first end to said second end.

2. The separation device of claim 1, wherein the fibers are physically fused to one another.

3. The separation device of claim 2, wherein the fibers are heat fused to one another.

4. The separation device of claim 1, wherein the fibers are chemically fused to one another.

5. The separation device of claim 1, wherein the plurality of fibers comprise fibers having a nominally circular cross-section.

6. The separation device of claim 1, wherein the plurality of fibers comprise fibers configured with a plurality of co-linear channels along the entire length of the surface of each fiber.

7. The separation device of claim 1, the separation device further comprising different polymeric fibers.

8. The separation device of claim 1, wherein the polymeric fibers have been modified to exhibit enhanced reactivity.

9. The separation device of claim 8, wherein the enhanced reactivity comprises enhanced attraction for a predetermined molecular species.

10. The separation device of claim 1, further comprising an instrument disposed at an end of the monolithic cartridge that is configured for detecting a molecular species in a fluid moving through the monolithic cartridge.

11. A liquid chromatography device comprising a monolithic cartridge having a first end and a second end and comprising a liquid chromatography stationary phase, the stationary phase comprising a plurality of nominally aligned polymeric fibers that exhibit a chemical affinity for a component of a liquid phase, wherein at least a portion of the fibers are directly fused to one another at points of contact along the fiber lengths such that the monolithic cartridge includes spot bonds located randomly throughout the entire length of the monolithic cartridge, the monolithic cartridge defining a plurality of capillaries capable of bulk wicking the liquid phase between adjacent fibers from said first end to said second end.

12. The separation device of claim 11, wherein the polymeric fibers have a nominally circular cross-section.

13. The separation device of claim 11, wherein the fibers are configured with a plurality of co-linear channels along the entire length of the surface of each fiber.

14. The separation device of claim 11, the separation device further comprising different polymeric fibers.

15. The separation device of claim 11, wherein the polymeric fibers have been modified to exhibit enhanced reactivity.

16. The separation device of claim 15, wherein the enhanced reactivity comprises enhanced attraction for a predetermined molecular species.

17. The separation device of claim 11, further comprising an instrument disposed at an end of the monolithic cartridge that is configured for detecting a molecular species in a fluid moving through the monolithic cartridge.

18. A liquid chromatography device comprising
a monolithic cartridge having a first end and a second end and comprising a plurality of nominally aligned polymeric fibers, wherein the polymeric fibers are the stationary phase of the liquid chromatography device and exhibit a chemical affinity for a component of a liquid phase, at least a portion of the fibers being directly fused to one another at points of contact along the fiber lengths such that the monolithic cartridge includes spot bonds located randomly throughout the entire length of the monolithic cartridge, the cartridge defining a plurality of capillaries capable of bulk wicking the liquid phase between adjacent fibers from said first end to said second end; and
an instrument disposed at an end of the monolithic cartridge that is configured for detecting a molecular species in a fluid moving through the monolithic cartridge.

19. The separation device of claim 18, wherein the fibers are heat fused to one another.

20. The separation device of claim 18, wherein the fibers are chemically fused to one another.

21. The separation device of claim 18, wherein the fibers are pressed together with radial compression forces to fuse the fibers and form the plurality of capillaries.

22. The separation device of claim 18, wherein the plurality of fibers comprise fibers having a nominally circular cross-section.

23. The separation device of claim 18, wherein the plurality of fibers comprise fibers configured with a plurality of co-linear channels along the entire length of the surface of each fiber.

24. The separation device of claim 18, further comprising different polymeric fibers.

25. The separation device of claim 18, wherein the polymeric fibers have been modified to exhibit enhanced reactivity.

26. The separation device of claim 25, wherein the enhanced reactivity comprises enhanced attraction for a predetermined molecular species.

27. The separation device of claim 18, the monolithic cartridge further comprising a wrap surrounding the plurality of fibers and disposed along the axial length of the aligned fibers.

* * * * *